(12) United States Patent
Van De Laar et al.

(10) Patent No.: US 10,085,660 B2
(45) Date of Patent: Oct. 2, 2018

(54) AUTOMATIC ANALYSIS OF UTERINE ACTIVITY SIGNALS AND APPLICATION FOR ENHANCEMENT OF LABOR AND DELIVERY EXPERIENCE

(71) Applicant: KONINKLIJKE PHILIPS N.V., Eindhoven (NL)

(72) Inventors: Jakob Van De Laar, Oosterhout (NL); Jeanine Johanna Maria Kierkels, Roermond (NL)

(73) Assignee: Koninklijke Philips N.V., Eindhoven (NL)

( * ) Notice: Subject to any disclaimer, the term of this patent is extended or adjusted under 35 U.S.C. 154(b) by 638 days.

(21) Appl. No.: 14/429,000

(22) PCT Filed: Sep. 19, 2013

(86) PCT No.: PCT/IB2013/058668
§ 371 (c)(1),
(2) Date: Mar. 18, 2015

(87) PCT Pub. No.: WO2014/045221
PCT Pub. Date: Mar. 27, 2014

(65) Prior Publication Data
US 2017/0319087 A1    Nov. 9, 2017

Related U.S. Application Data

(60) Provisional application No. 61/702,966, filed on Sep. 19, 2012.

(51) Int. Cl.
*A61B 5/103*    (2006.01)
*A61B 5/117*    (2016.01)
(Continued)

(52) U.S. Cl.
CPC ............... *A61B 5/033* (2013.01); *A61B 5/03* (2013.01); *A61B 5/04882* (2013.01); *A61B 5/4356* (2013.01); *G06F 3/0482* (2013.01)

(58) Field of Classification Search
CPC ... A61B 5/02411; A61B 5/08; A61B 2503/02; A61B 5/0011; A61B 5/033; A61B 5/04
(Continued)

(56) References Cited

U.S. PATENT DOCUMENTS 4,711,585 A    12/1987    Fresquez et al.
6,302,849 B1    10/2001    Shine et al.
(Continued)

FOREIGN PATENT DOCUMENTS

EP    1181890 A1    2/2002
EP    1852060 A1    11/2007
(Continued)

OTHER PUBLICATIONS

Rijnders et al, "Perinatal Factors Related to Negative or Positive Recall of Birth Experience in Women 3 Years Postpartum in the Netherlands" Birth . Chapter 2, 2008, pp. 17-36.
(Continued)

*Primary Examiner* — May Abouelela

(57) ABSTRACT

A uterine activity analysis apparatus, comprising a rendering device at least one controller coupled to the rendering device, and configured to acquire a uterine activity signal (UAS) corresponding to uterine activity of a patient; determine uterine activity information based upon the acquired UAS and render, on the rendering device, content based at least in part including UAS upon the determined uterine activity information. The controller may compare the determined uterine activity information with threshold uterine activity information and provide clinical decision support (CDS) based upon the decision. Furthermore, the controller
(Continued)

may render a breathing guide to illustrate a preferred breathing pattern, when the start of a contraction is detected.

21 Claims, 8 Drawing Sheets

(51) Int. Cl.
G08B 1/00 (2006.01)
G08B 25/00 (2006.01)
A61B 5/03 (2006.01)
A61B 5/00 (2006.01)
A61B 5/0488 (2006.01)
G06F 3/0482 (2013.01)

(58) Field of Classification Search
USPC ......... 600/300, 558, 301, 587, 588; 340/309
See application file for complete search history.

(56) References Cited

U.S. PATENT DOCUMENTS

| 6,421,558 | B1 | 7/2002 | Huey et al. | |
|---|---|---|---|---|
| 9,532,745 | B2* | 1/2017 | Jeanne | A61B 5/4356 |
| 2005/0267376 | A1 | 12/2005 | Marossero et al. | |
| 2006/0015036 | A1* | 1/2006 | Paltieli | A61B 17/42 |
| | | | | 600/558 |
| 2006/0282019 | A1* | 12/2006 | Hamilton | A61B 5/00 |
| | | | | 600/591 |
| 2008/0027357 | A1* | 1/2008 | Owen | A61B 17/42 |
| | | | | 600/588 |
| 2008/0319472 | A1 | 12/2008 | Shelley | |
| 2010/0030089 | A1* | 2/2010 | Hyde | G06F 19/3456 |
| | | | | 600/508 |
| 2011/0144458 | A1 | 6/2011 | Gauta | |
| 2014/0249383 | A1* | 9/2014 | Jeanne | A61B 5/4356 |
| | | | | 600/301 |

FOREIGN PATENT DOCUMENTS

| RU | 2228711 C1 | 5/2004 |
|---|---|---|
| WO | 2005096707 A2 | 10/2005 |

OTHER PUBLICATIONS

Rouhe et al, "Fear of Childbirth According to Parity, Gestational Age, and Obstetric History" Bjog 2009; vol. 116, pp. 67-73.
Hodnett Ed et al "Continuous Support for Women During Childbirth (Review)." The Cochrane Collaboration, 2011 pp. 1-114.
Ford et al, "Creating Customer-Focused Health Care Organizations", Health Care Management Review, vol. 25, No. 4, 2000, pp. 18-33.
Goodman et al, "Issues and Innovations in Nursing Practice: Factors Related to Childbirth Satisfaction", Journal of Advanced Nursing, vol. 46, 2004, pp. 212-219.
Buitendijk, De Stem Van Vroede Vrouwen (The Voice of Vroede Women), University of Amsterdam, March 12, 2010, pp. 1-22.

* cited by examiner

500

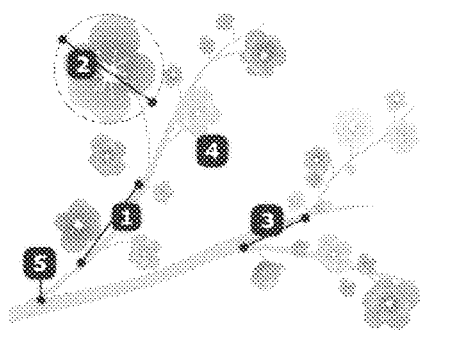
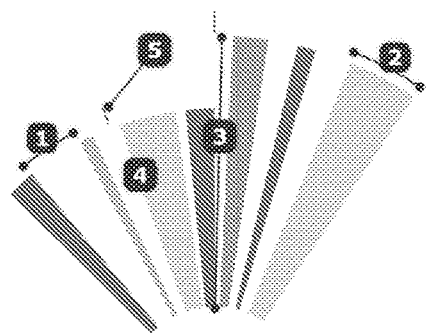
FIG. 7                  FIG. 8

AUTOMATIC ANALYSIS OF UTERINE ACTIVITY SIGNALS AND APPLICATION FOR ENHANCEMENT OF LABOR AND DELIVERY EXPERIENCE

CROSS-REFERENCE TO PRIOR APPLICATIONS

This application is the U.S. National Phase application under 35 U.S.C. § 371 of International Application No. PCT/IB2013/058668, filed on Sep. 19, 2013, which claims the benefit of U.S. Provisional Patent Application No. 61/702,966, filed on Sep. 19, 2012. These applications are hereby incorporated by reference herein.

The present system relates to a system which analyzes uterine activity signals (UASs) and, more particularly, to a system which analyzes UASs, extracts parameters as well as state information from these UASs, generates content based upon the extracted parameters and state information, and thereafter renders the generated content, and a method of operation thereof.

Typically, during a childbirth process (e.g., or other labor or birthing process) it is desirable to provide support to an expectant mother (e.g., hereinafter a patient or expectant unless the context indicates otherwise) to comfort her and/or to assist her during the childbirth process. Typical breathing support systems provide breathing support based upon information manually input by, for example the patient or a professional such as a doctor, nurse, midwife, etc. For example, in U.S. Pat. No. 4,711,585, the contents of which are incorporated herein by reference, shows a system which requires manual input of information by the patient in order to synchronize the system with the patient's contractions. Unfortunately, this process is inconvenient.

Typically, uterine activity signals (UASs) may be obtained using a tocodynamometer (toco), which outputs a tocogram, an Intrauterine Pressure Catheter (IUPC), which outputs an intrauterine pressure signal, and/or a device for measuring an electrohysterogram (EHG). Thereafter, analysis and interpretation of a uterine activity signal may be manually performed by human experts. This is a labor-intensive, error-prone, and subjective process. Further, when using a tocodynamometer to generate the UASs, professionals monitoring the signal must regularly check to assure that the signal does not run off-scale, which may occur when the amplitude of the contractions or the baseline offset is very large. If this occurs (e.g., the signal runs off-scale), the professionals must manually switch to a larger scale. Obviously, the professionals must also check regularly whether the opposite scenario has occurred. Several other Clinical Decision Support (CDS) applications of the information provided by the algorithm are possible. For example, as described in U.S. Pat. No. 6,302,849, the contents of which are incorporated herein by reference, initiation or continuation of maternal blood pressure measurement may be prevented when there is significant uterine activity.

It is known that providing support to an expectant mother during the birthing process may reduce fear and stress and contribute to a positive childbirth experience (see, Rijnders M, Baston H, Schönbeck Y, van der Pal K, Prins M, Green J, Buitendijk S. Perinatal factors related to negative or positive recall of birth experience in women 3 years postpartum in the Netherlands. Birth 2008 June; 35(2):107-16, the entire contents of which is incorporated herein by reference thereto). Further, as it is known that fear during the birthing process may lead to several undesirable physiological effects such less effective uterine contractions, a prolonged active labor, and/or abnormal fetal heartbeats, it is desirable to provide the expectant mother with an environment which may reduce this fear so as to facilitate normality of birth (see, Rouhe H, Salmela-Aro K, Halmesmäki E, Saisto T. Fear of childbirth according to parity, gestational age, and obstetric history. BJOG 2009; 116: 67-73, the entire contents of which is incorporated herein by reference thereto).

Moreover, in today's competitive healthcare market, it is desirable to improve quality-of-care (QoC) and provide value added services so as to differentiate one healthcare provider from another. As a result of this competitive healthcare market, the focus of perceived user value will have to include patients' experiences and comfort next to functionality (see, Ford R C, Myron D. Creating Customer-focused Health Care Organizations. Health Care Management Review 2000; 25(4):18-33, the entire contents of which is incorporated herein by reference thereto). In obstetrics, this trend has focused on women's experiences of childbirth. A delivery is one of the major events in life: a radical experience that evokes strong emotions. A good delivery experience is crucial for the woman's wellbeing, health and relationship with her infant (see, Goodman P, Mackey M C, Tavakoli A S: Issues and innovations in nursing practice: Factors related to childbirth satisfaction. Journal of Advanced Nursing 2004; 46:212-219, the entire contents of which is incorporated herein by reference thereto; Buitendijk S E. Vrouwen moeten zeggenschap terugkrijgen over bevalling. De stem van vroede vrouwen. Oratie Geneeskunde van mw. Prof. dr. S. E. Buitendijk, bijzonder hoogleraar Eerstelijns Verloskunde en Ketenzorg, the entire contents of which is incorporated herein by reference thereto).

Rijnders concluded in her study that a substantial proportion of Dutch women looked back negatively on their birth giving experience three years postpartum (see, Rijnders 2008). One conclusion of her study is that continuous support during labor contributes to improve birth experiences of women, because continuous support may reduce fear and stress. It is known that fear of childbirth may lead to less effective uterine contractions, abnormal fetal heart beat and a prolonged active labor. So reducing fear may result in facilitating normality of birth (see, Rouhe 2009).

Furthermore, a recent Cochrane review shows that continuous support during labor leads to significantly more vaginal births, less cesarean deliveries and less instrument assisted deliveries (see, Hodnett E D, Gates S, Hofmeyr G J, Weston J. "Continuous support for women during childbirth (Review)." The Cochrane Collaboration, 2011, the entire contents of which is incorporated herein by reference thereto). In practice, one-on-one support is typically not achievable because of logistic and financial reasons.

It is an object of the present system to overcome disadvantages and/or make improvements in the prior art.

It is a further object of some embodiments of the present system to provide support wherein physiological monitoring is performed to contribute to an improved experience and/or to provide clinical support.

The system(s), device(s), method(s), user interface(s), computer program(s), processes, etc. (hereinafter each of which will be referred to as system, unless the context indicates otherwise), described herein address problems in prior art systems.

Embodiments of the present system may include an algorithm which may analyze a uterine activity signal (UAS) such as obtained with a conventional tocodynamometer, IUPC, or an EHG device. Embodiments of the present system may then process the UAS to determine information about uterine activity such as the start, peak and end times of contractions, time intervals between them, durations, intensities, timing patterns, waveform shapes, and so forth. Then, a graphical and/or textual representation of the determined uterine activity parameters and state information may be formed and rendered for the convenience of a user and/or for providing clinical information to a clinician, etc. Further, information generated by embodiments of the present system may be stored in a memory of the system for later use.

In accordance with embodiments of the present system there is disclosed a uterine analysis apparatus which may include a rendering device; and at least one controller coupled to the rendering device which may be configured to: acquire a uterine activity signal (UAS) corresponding to uterine activity of a patient; determine uterine activity information based upon the acquired UAS; and render, on the rendering device, content based at least in part upon the determined uterine activity information. It is further envisioned that the at least one controller may be further configured to form the content in accordance with a selected uterine activity representation theme. The at least one controller may be further configured to compare the determined uterine activity information with threshold uterine activity information and provide clinical decision support (CDS) based upon the decision. It is also envisioned that the uterine activity information may include information related to at least one parameter or state of the acquired UAS.

Moreover, the at least one controller may be configured to render a menu including a plurality of uterine activity representation themes for selection by a user. It is further envisioned that the at least one controller may be configured to render a breathing guide to illustrate a preferred breathing pattern, for example when the start of a contraction is detected and/or may be started manually when desired.

In accordance with yet other embodiments of the present system, there is envisioned a method of rendering content related to uterine activity of a patient, the method may be performed by at least one controller of a system and may include one or more acts of: acquiring a uterine activity signal (UAS) corresponding to uterine activity of a patient; determining uterine activity information based upon the acquired UAS; and rendering, on a rendering device, content based at least in part upon the determined uterine activity information. The method may further include an act of forming the content further in accordance with a selected uterine activity representation theme.

Moreover, the method may include an act of comparing the determined uterine activity information with threshold uterine activity information and provide clinical decision support (CDS) based upon the decision. For example, if an amplitude of a determined uterine activity parameter information exceeds a threshold amplitude, the process may sound an alarm. It is also envisioned that the method may further include an act of forming the uterine activity information to comprise information related to at least one parameter of the acquired UAS. The method may further include an act of rendering a menu including a plurality of uterine activity representation themes for selection by a user. The method may also include an act of rendering a breathing guide to illustrate a preferred breathing pattern, when the start of a contraction is detected.

In accordance with yet other embodiments of the present system, there is disclosed a computer program stored on a computer readable memory medium, the computer program configured to render on a rendering device content related to uterine activity of a patient, the computer program may include a program portion configured to: acquire a uterine activity signal (UAS) corresponding to the uterine activity of the patient; determine uterine activity information based upon the acquired UAS; and render, on the rendering device, content based at least in part upon the determined uterine activity information. The program portion may be further configured to form the content further in accordance with a selected uterine activity representation theme. Moreover, the program portion may be further configured to compare the determined uterine activity information with threshold uterine activity information and provide clinical decision support (CDS) based upon the decision. It is also envisioned that the program portion may be further configured to form the content further in accordance with the selected uterine activity representation theme.

It is further envisioned that the program portion may be further configured to render a menu including a plurality of uterine activity representation themes for selection by a user. It is also envisioned that program portion is further configured to render a breathing guide to illustrate a preferred breathing pattern, when the start of a contraction is detected.

In accordance with embodiments of the present system, there is disclosed a data visualization feedback method, comprising: acquiring a signal related to a physiology of a patient; determining at least one parameter of the signal over a time period; determining a change in the signal over the time period; forming content based upon the determined change of the signal; and rendering the content.

The invention is explained in further detail, and by way of example, with reference to the accompanying drawings wherein:

FIG. 7 is a graph illustrating content rendered in accordance with embodiments of the present system;

FIG. 8 is a graph illustrating a portion content rendered in accordance with embodiments of the present system.

Figure 1:
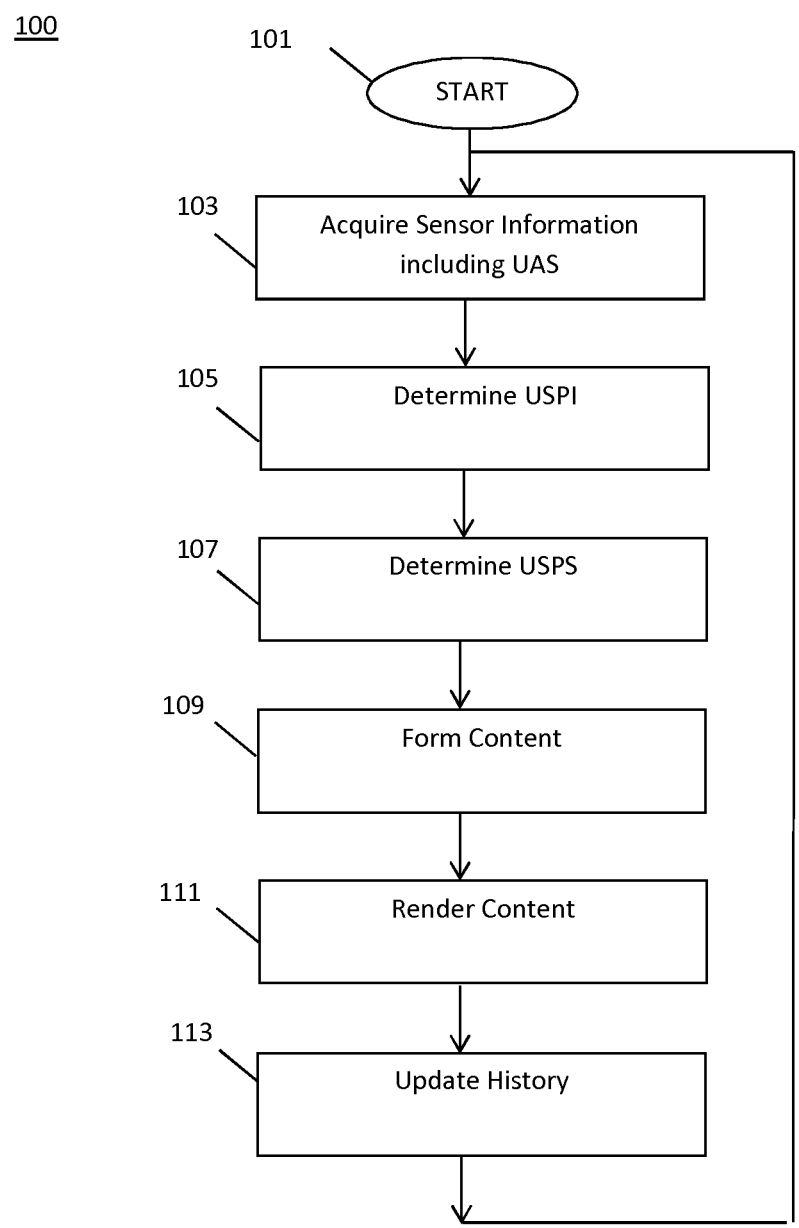
FIG. 1 is a flow diagram that illustrates a process performed by a system in accordance with embodiments of the present system.

The following are descriptions of illustrative embodiments that when taken in conjunction with the following drawings will demonstrate the above noted features and advantages, as well as further ones. In the following description, for purposes of explanation rather than limitation, illustrative details are set forth such as architecture, interfaces, techniques, element attributes, etc. However, it will be apparent to those of ordinary skill in the art that other embodiments that depart from these details would still be understood to be within the scope of the appended claims. Moreover, for the purpose of clarity, detailed descriptions of well-known devices, circuits, tools, techniques and methods are omitted so as not to obscure the description of the present system. It should be expressly understood that the drawings are included for illustrative purposes and do not represent the entire scope of the present system. In the accompanying drawings, like reference numbers in different drawings may designate similar elements.

The term rendering and formatives thereof as utilized herein refer to providing content, such as for visualization or Clinical Decision Support (CDS), such that it may be perceived by at least one user sense, such as a sense of sight. For example, the present system may render a user interface on a display device, a wall (such as by projecting the user interface on the wall), etc., so that it may be seen, interacted with and/or otherwise perceived by a user. The term rendering may also comprise all the actions required to generate the display of content, whether it be graphical, textual, etc., on a display device.

The present system is directed to monitoring of physiological conditions, whether the monitoring be performed in a clinical environment, be home-based, such as home-based monitoring of labor, etc. However, while the following will illustratively be described with regard to physiological conditions (e.g., uterine activity) during labor, it should be expressly understood that the present system is also applicable to other healthcare areas, such as those that are characterized by longer-term processes, treatments and/or monitoring. For example, the present system may be suitably applied in complex contexts where different physiological parameters are collected and/or patients undergo a physically unpleasant or emotional tough experience. In these situations, the data visualization feedback may help to improve the patient experience and/or treatment by providing additional insight and/or positive encouragement in a more understandable and comforting manner. The present system may also be suitably applied to assisting oncology patients receiving chemotherapy, family members and/or clinicians involved in such treatment, patients receiving (hemo)dialysis treatment, family members and/or clinicians involved in such treatment, patients (women) experiencing infertility problems, family members and/or clinicians involved in such treatment/monitoring; monitoring of intensive care patients, family members and/or clinicians involved in such treatment/monitoring, monitoring of patients with a chronic illnesses like diabetes, fibromyalgia, or multiple sclerosis (MS) and the like.

For the simplicity of the following discussion, the present system will be described with regard to the monitoring of uterine activity during child birth. However, it should be expressly understood that this illustrative discussion should be understood to encompass each of the above and others where the present system may be suitably applied.

FIG. 1 is a flow diagram that illustrates a process 100 performed by a system in accordance with embodiments of the present system. The process 100 may be performed using one or more computers that may communicate over a network and may obtain information from, and/or store information to one or more memories which may be local and/or remote from each other. The process 100 may include one or more of the following acts. Further, one or more of these acts may be combined and/or separated into sub-acts, if desired. Further, one or more of these acts may be skipped depending upon settings. In operation, the process may start during act 101 and then proceed to act 103.

During act 103, the process may acquire sensor information. The sensor information may include information related to uterine activity of a patient and/or other information related to the patient. For example, the sensor information may include a uterine activity signal (UAS) including information related to uterine activity of the patient. In accordance with some embodiments, the UAS may be a tocogram, an intrauterine pressure signal (IUPC), an electrohysterogram (EHG), etc., and/or combinations thereof. In accordance with embodiments of the present system, the UAS may be formed and/or processed in real time. However, in yet other embodiments the UAS may be delayed, stored (e.g., in a memory of the system), and/or processed at a later time.

Figure 4:
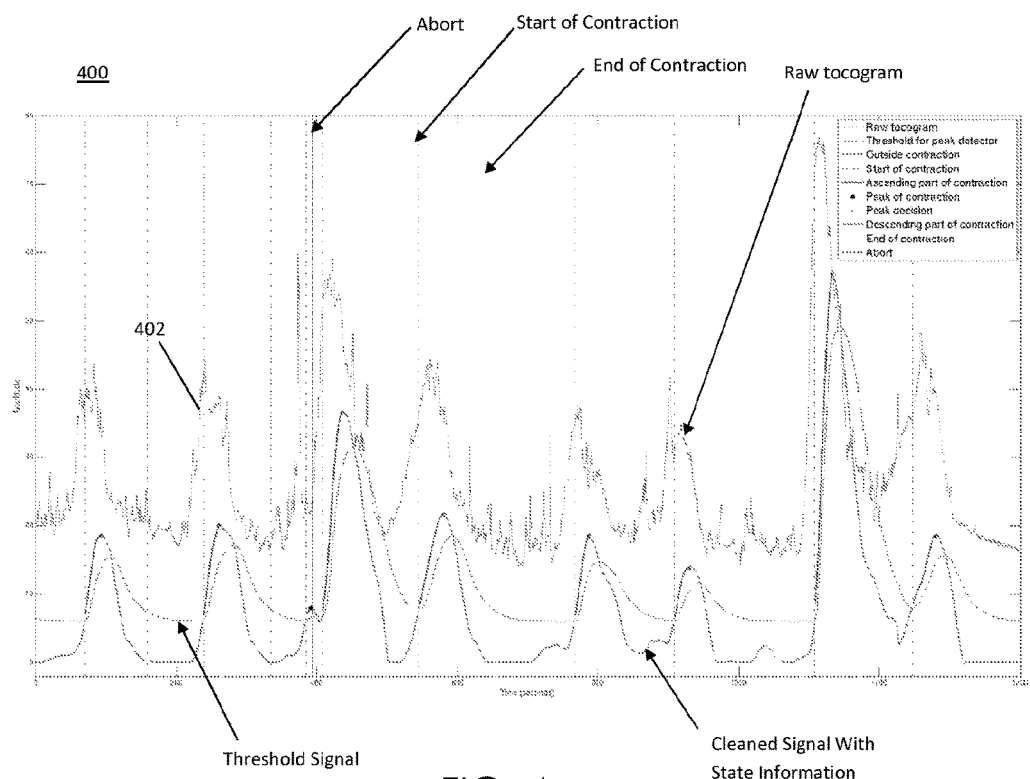
FIG. 4 is a graph showing information generated in accordance with embodiments of the present system.
Figure 5:
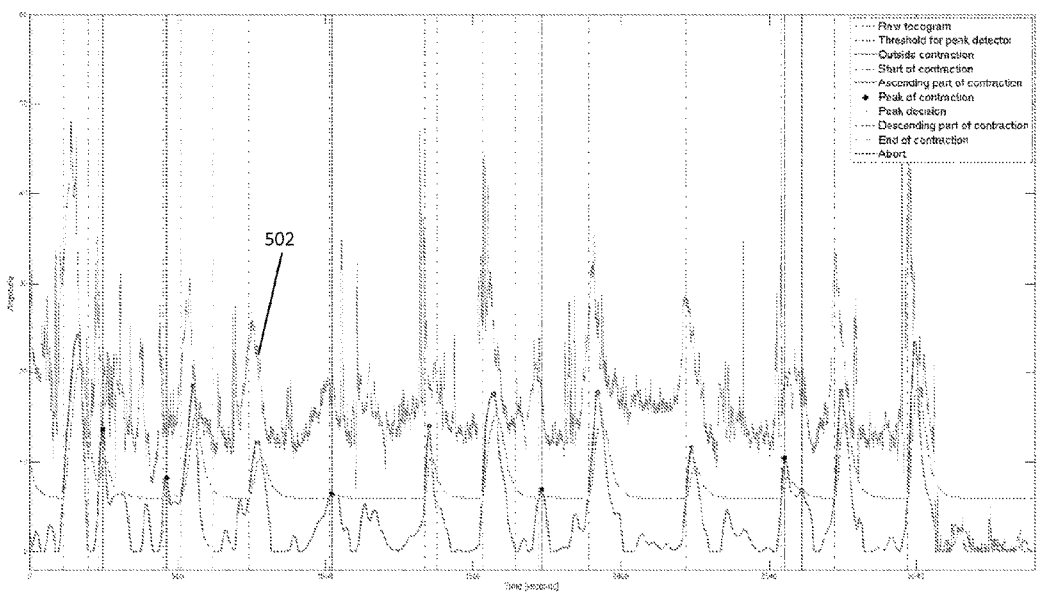
FIG. 5 is a graph showing information generated in accordance with embodiments of the present system.

The UAS may contain many large artifacts, which often are due to movement of the patient, such as movement due to breathing or changing position, and may resemble an impulse (e.g., a spike) especially when the UAS includes one or more signals generated by a tocodynamometer (e.g., a tocogram), but such artifacts may also occur in IUPC and EHG signals. UASs obtained in accordance with embodiments of the present system are shown in FIGS. 4 and 5 which are graphs 400 and 500, respectively, showing information generated in accordance with embodiments of the present system. For example, FIGS. 4 and 5 each include UASs 402 and 502, respectively, each of which is a raw tocogram (i.e., a raw UAS) generated in accordance with embodiments of the present system.

When UASs, such as UASs 402 and 502, are generated for example by a tocodynamometer or other device, small movements of the patient may induce noise such as spikes and/or other large artifacts in these signals. Further, monitored signals such as the UASs 402 and 502 may have a large and/or varying (e.g., changing) baseline offset. For example, the baseline offset may substantially vary (change) whenever the patient moves and/or changes position. After completing act 103, the process may continue to act 105.

During act 105, the process may determine UAS parameter information (USPI) in accordance with the UAS. The USPI may include a threshold signal, derivative signal(s) (e.g., smoothed derivative(s) of first and/or second order with respect to time), moving percentile information (MPI) (e.g., moving percentiles) and baseline jump detection information (BJDI), and cleaned signal information. This information and methods to derive this information will be discussed with respect to the process shown in FIG. 2.

In accordance with some embodiments, the process may clean the UAS so that information such as a cleaned signal, a threshold signal, derivatives, etc. may be extracted therefrom. The process may clean the UAS so that, for example, noise such as spikes, impulses, etc., and/or baseline offset, etc., may have a reduced effect on the analysis and interpretation of the UAS. For example, with regard to change of the baseline offset of the UAS, a sudden increase or decrease of the baseline offset may be confused with a start or an end of a contraction. In addition, without proper processing, the reliability of various estimates such as the intensity of the detected contractions may be compromised. Hence, during act 105 an estimate of the baseline offset is subtracted from the signal. Further, a sudden increase and/or decrease of the baseline offset may cause the UAS to run off-scale. Accordingly, during act 105, the process may subtract an estimate of the baseline offset from the UAS to get an estimated UAS signal with baseline offset removed (for simplicity referred to simply as UAS). After completing act 105, the process may continue to act 107.

During act 107, the process may determine UAS contraction parameters and/or state information (USPS) which may include information related to a current parameter and/or state of the UAS such as, one or more of start, peak, and end times (of contractions), time between contractions, duration (of contractions), and a cleaned signal. At least part of the USPS may be determined using a peak detector state machine (PDSM) which may determine the USPS based upon one or more of the USPI and the UAS. A process to perform real-time or offline peak detection and determine the USPS is discussed with reference to FIG. 3. With reference to FIGS. 4 and 5, the parameter and state information (e.g., included in the USPS) extracted by the PDSM may, for example, include information such as is listed in Table 1 as will be described with reference to FIGS. 2 and 3 below.

TABLE 1

USPS PARAMETERS AND/OR STATES (uterine activity information)

| Extracted information (on legend) | Ref. Name |
|---|---|
| Outside contraction | Outside |
| Start of contraction | Start |
| Ascending part of contraction | Ascending |
| Peak of contraction | Peak |
| Peak decision | PeakDcs |
| Descending part of contraction | Descending |
| End of contraction | End |
| Abort | Abort |

With regard to acts 105 and 107, in accordance with some embodiments, the process may analyze the UAS and extract desired uterine activity information from the UAS. The uterine activity information may include information related to the USPS, uterine activity states, etc.

With regard to acts 105 and 107, during a first filtering act, artifacts in the UAS may be suppressed significantly by (weighted) median, (weighted) order statistic, decision-based, or other nonlinear filtering followed by smoothing with a linear and/or nonlinear smoothing filter or filters. If linear filtering were performed using a low-pass filter as a first filtering act, then artifacts in the UAS would smear out in time instead of being suppressed. Due to the particular characteristics of noise in a UAS, which typically is non-Gaussian and asymmetric, nonlinear filters may provide better suppression of the noise than linear Finite Impulse Response (FIR) or Infinite Impulse Response (IIR) filters may provide. For example, toco-generated UAS signals include a greater number of positive than negative noise spikes. Accordingly, a nonlinear filter such as a weighted-order statistic filter may take into account such an asymmetry while better preserving the desired signal characteristics than may be performed using linear filters.

Further, embodiments of the present system may include a detector to detect jumps in the baseline offset. This detector may be based on the fact that the levels of the UAS before and after a jump differ significantly while the variance of the signal on either side is relatively small.

Further, embodiments of the present system may include a detector to detect whether the acquired UAS needs to be scaled (e.g. when it runs off-scale or when it is very small during strong contractions) and an automatic scale adjuster may be triggered based on the output of the detector.

The large variability in contractions makes proper peak detection and extraction (e.g., substantially in real-time) of uterine activity parameters difficult. Accordingly, embodiments of the present system may employ one or more algorithms which cope with this fact by computing an intermediate signal such as a threshold signal that is a smoothed version of the cleaned UAS (see FIG. 2). Further, in accordance with some embodiments parameters extracted by the process may further aid in the interpretation of fetal heart rate (HR) traces in a clinical setting.

After completing act 107, the process may continue to act 109.

Figure 6:
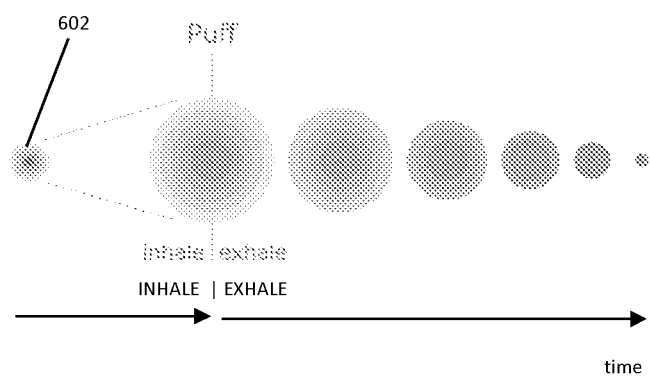
FIG. 6 is a graph illustrating content rendered in accordance with embodiments of the present system.

During act 109, the process may form content corresponding to the determined USPS. The content may be formed using any suitable graphics generator process (generally a graphics process which may be performed by a graphics application (GA)) which may be programmable by the system and/or user, if desired. The content may include information, such as text and/or graphics, which may be used to render a representation of at least part of the USPS such as start, peak and end times of one or more contractions, the time between two (adjacent) contractions, duration of one or more contractions, as well as information related to dilation progress, and internal examination moment. With regard to the information related to the dilation progress and the internal examination moment, this information may be manually entered, by a professional such as a doctor, etc. For example, FIGS. 6 through 8 show content formed in accordance with the USPS by a graphics application (GA) and may be rendered in accordance with embodiments of the present system. The GA may generate content which may include information suitable for rendering a visualization of the progression of labor and/or provide labor breathing support. This content may further include information related to audio and/or visual data, graphic information, etc. and may be formed in accordance with a system and/or user-defined theme.

For example, in accordance with embodiments of the present system, the visualization of the progression of labor may include information related to uterine activity such as the start, peak and/or end times of contractions, the time intervals between them, their durations, intensities, timing patterns, waveform shapes, etc. each of which may be rendered (independently and/or in association with other information) to visualize the progress of the patient during labor in real-time or offline mode. This way, the GA may generate content corresponding to the UAS, USPS, and/or USPI which may be used to form a unique (data) visualization for each patient. The content may be further personalized in accordance with default settings and/or patient settings. For example, a user (e.g., a patient and/or partner of the patient, a professional, etc.) may further personalize the visualization by e.g. choosing their preferred theme and colors selected from a plurality of themes and/or colors available. Moreover, to provide breathing support the content may be formed to provide real-time support for the convenience of the patient. For example, during labor the content may include a visual breathing guide which may provide real-time support to the patient to assist for example in pattern breathing exercises to help with patient focus and reduce pain during contractions. Further, the GA may form the content so that automatic synchronization to a patient's contractions may be made possible. Further, the breathing guide may include one or more labor breathing techniques for adequate support during the different stages of labor as may be automatically selected or selected by a user. Information related to the one or more labor breathing techniques may be stored in a memory of the system and may be selected as desired. Further, the process may start a breathing guide for the convenience of a user for example when the start of a contraction is detected, if desired. Further, with regard to the breathing guide, the breathing guide may be generated in accordance with a representation/visualization theme which may be selected by the user and/or system. Accordingly, a menu including a plurality of breathing guide representation themes for selection by the user may be rendered by the process for selection by the user. After completing act 109, the process may continue to act 111.

During act 111, the content may be rendered such as for example displayed by any suitable display of the system such as a monitor and/or projector. Accordingly, the content may be displayed on, for example, a wall of a delivery room, a portable display device, etc., if desired. The patient, the patient's partner and/or professionals (e.g., midwife, doctors, nurses, caretakers, etc.) may tune the breathing guide exercises to be performed by the patient by, for example, indicating timing (e.g., breathing rate, etc.) and behavior. Further, users such as the patient, etc. may interact with embodiments of the present system to personalize the breathing guide by, for example, selecting their preferred theme and/or color(s) as described further herein. Thus, using the rendered information, the patient, partner and/or professionals (e.g., midwife, doctors, nurses, caretakers, etc.) may tune the breathing exercises performed by the patient by, for example, indicating timing and behavior. The process may continually repeat acts of the process 100 until it is requested to end (e.g., by the system and/or user). Further, the parameters may include corresponding confidence levels, if desired. These confidence levels may be indicative of a computed accuracy for each variable of the UAS parameter signals.

FIGS. 6 through 8 are graphs illustrating content rendered in accordance with embodiments of the present system. With reference to FIG. 6, in accordance with a theme for rendering a breathing guide, the content rendered may include a series of animated roundels 602 (e.g., animated circles) which may function as a breathing guide and may be rendered serially (in time). The breathing guide may be started for example when a (strong) contraction is detected (e.g., a contraction that is greater than or equal to a contraction threshold). However, in yet other embodiments, if desired, the breathing guide may be started manually by the patient and/or in response to other detected parameters, conditions, etc. For example, the roundels may grow (e.g., increase in diameter using shaded rings or the like) to indicate when a patient should inhale and may contract to indicate that the patient should exhale. Thus, the breathing guide may illustrate a preferred breathing pattern. Each of the animated circle(s) may provide information to a patient to inform the patient of when to breath so as to establish a desired rhythm. Further, colors of the animated roundels 602 may change to indicate inhalation or exhalation acts.

Further, graphics such as lines, arrows, alphanumerical characters (e.g., letters, words (e.g., Puff, inhale, exhale, etc.)) arrows, etc. may be generated and/or rendered for the convenience of the user(s).

With reference to FIG. 7, in accordance with a theme for visualization of the progression of labor, the content may include a series of information items such as branches, flowers, and/or a legend. This content may include a mapping of the USPS of a patient (e.g., during labor or possible labor) and may grow over the course of labor. For example, a distance between branches (see numeral 1, FIG. 7) of a first stalk may indicate for example a time between two contractions, for example with the longer the time between contractions, the longer this distance. In this embodiment, conversely, the shorter the time between contractions, the shorter this distance. The duration of a contraction (see numeral 2, FIG. 7) may be indicated by a rendering of a flower with the longer the duration of a contraction, the larger the flower and vice versa. A distance between branches on another stalk (see 3, FIG. 7) may indicate the dilation. The dilation progress may be indicated using a separate branch and may be sized in accordance with the dilation. The larger the dilation, the longer this distance and vice versa. The intensity of a contraction may be illustrated using color. For example, a color of a (current) flower may change from a light color to a dark color to indicate the intensity of a current contraction. For example, the darker the color, the greater the intensity of the contraction and vice versa. A visualization of an internal examination may be provided for example by an addition of a new branch (see 5, FIG. 7). In this way, the process may generate new flowers, stalks, branches, etc., in real time such that a display area may fill with the passing of time during labor.

With reference to FIG. 8, in accordance with yet another theme, the content may be provided in a form of a graph including a series of bars and/or a legend. A distance between adjacent bars (see 1, FIG. 8) may indicate a time between two contractions with the longer the time between contractions, the longer this distance and vice versa. A thickness of each bar may indicate a duration of a contraction (see 2, FIG. 8) with the longer the duration of a contraction, the wider the bar and vice versa. The length of each bar (see 3, FIG. 8) may be utilized to visualize an amount of uterine dilation wherein as the dilation progresses, the length of a corresponding bar increases accordingly. Thus, in accordance with embodiments of the present system, the larger the dilation, the larger the length of each bar and vice versa. The intensity of a contraction may be illustrated using color. For example, a color of a (current) bar may change from a light color to a dark color to indicate the intensity of a current contraction with for example, the darker the color, the greater the intensity of the contraction and vice versa. An internal examination moment may be visualized with an indicator (see 5) separating one series of bars from another series of bars.

After completing act 111, the process may continue to act 113 where the process may store information generated by the process such as the UAS(s), the determined USPI and USPS, the content, and/or the selected theme for later use. Accordingly, after the delivery, the content may be stored for later use such as a memento of the birth. The process may then repeat (e.g., to generated more graphic information) or may end, if desired.

In accordance with other embodiments of the present system, different mappings of uterine activity parameters (e.g., UAS parameters) to visualization are possible as may be set by the system and/or user. Further, in yet other embodiments, computer-generated graphics or other media forms such as light, sound, haptics, scents, etc., may be used to map the uterine activity parameters and, thus, to communicate the progress of labor to users such as professionals (e.g., doctors, nurses, midwives, etc.) and/or the patient.

Figure 2:
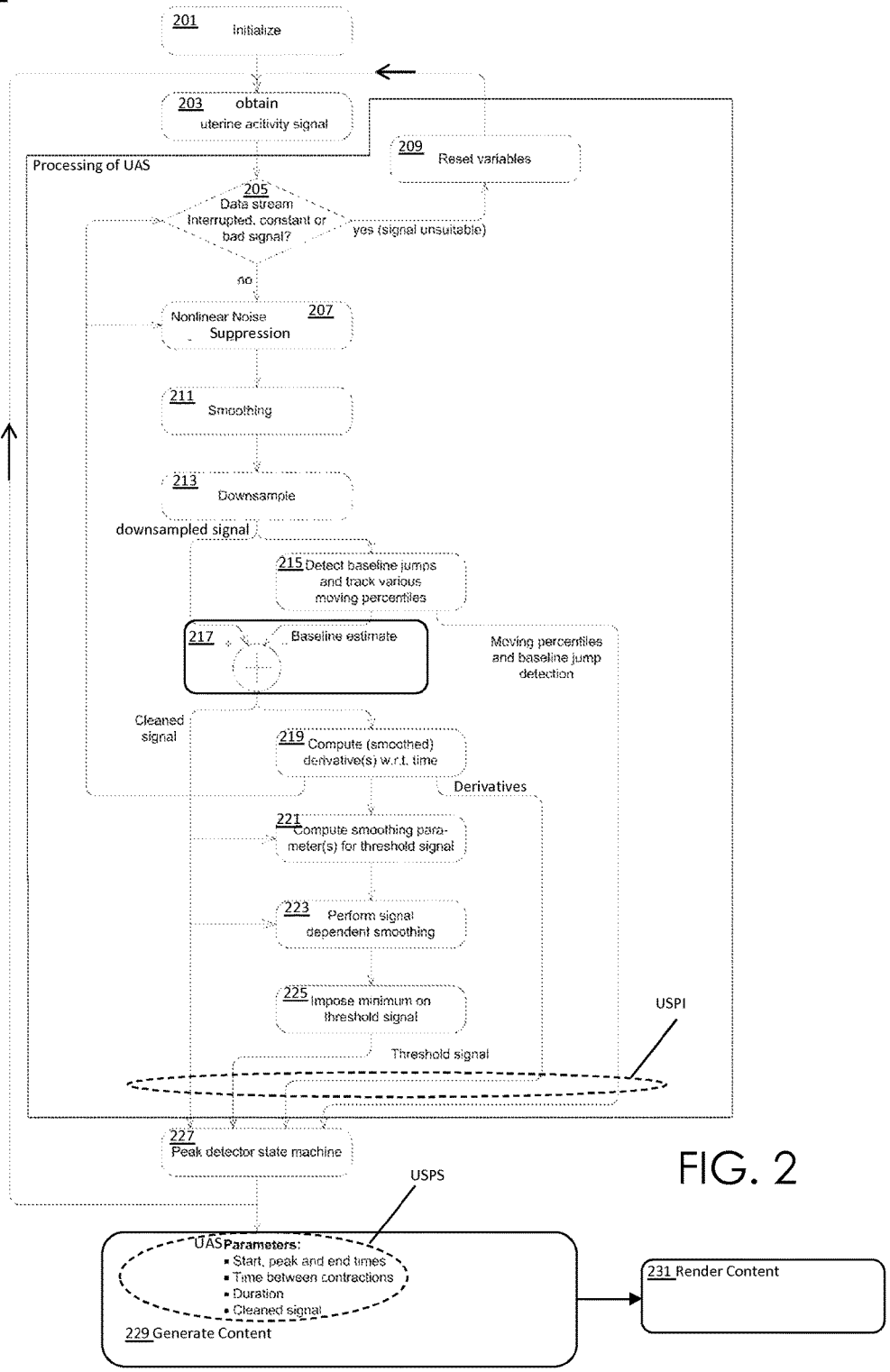
FIG. 2 is a flow diagram that illustrates a process performed by a system in accordance with embodiments of the present system.

FIG. 2 is a flow diagram that illustrates a process 200 performed by a system in accordance with embodiments of the present system. The process 200 may be performed using one or more computers that may communicate over a network and may obtain information from, and/or store information to one or more memories which may be local and/or remote from each other. The process 200 may include one of more of the following acts. Further, one or more of these acts may be combined and/or separated into sub-acts, if desired. Further, one or more of these acts may be skipped depending upon settings. During act 201, the process may perform an initialization process and may initialize algorithmic parameters (APs) and/or allocate memory buffers. Table 2 below illustrates exemplary settings of some of the APs in accordance with embodiments of the present system. However, the APs may include other values and/or ranges for the settings as may be set by the system and/or user, if desired. Further, other APs may be used.

TABLE 2

| Algorithmic Parameter (AP) | Description (times are in seconds) |
| --- | --- |
| T_cst (20) | If the signal is constant for this time, then this is detected and handled; used in 205 |
| T_nlns (17) | Duration of window for applying nonlinear noise suppression to raw data; used in 207 |
| T_sm (7) | Duration of the finite impulse response for smoothing, used 211 |
| T_prct_x (X) | Duration of the window for computing local percentile (multiple purposes and values); used among other things in 215 |
| T_mu_slope (5) | Duration of window for computing local smoothed slope; used in 219 |
| s_pk_min (10) | Minimum value for signal value at peak minus signal value at start; used in PDSM |
| z_min (5) | Minimum value imposed on the threshold signal; used in 225 |
| T_asc_min (15) | Minimum ascending time; if "true peak" is found earlier, then the current contraction candidate is aborted; used in PDSM |
| T_asc_max (100) | Maximum ascending time in seconds; if "true peak" is not found earlier, then the current contraction candidate is aborted; used in PDSM |
| T_desc_min (5) | Minimum descending time in seconds; if "true end" is found earlier, then the current contraction candidate is aborted; used in PDSM |
| T_desc_max (100) | Maximum descending time in seconds; if "true end" is not found earlier, then the current contraction candidate is aborted and a decision is made about whether or not it is a "true peak" (useful for eliminating small local peaks during ascending portion); used in PDSM |
| T_DP (1): | Peak Decision time, i.e., the time between a peak candidate is detected and when a decision is made about whether or not it is a "true peak" (useful for eliminating small local peaks during ascending); used in PDSM |
| T_DE (1): | End Decision time, i.e., the time between an end candidate is detected and when a decision is made about whether or not it is a "true end" (useful for eliminating small local peaks during descending portion); used in PDSM |

With reference to Table 2, the (exemplary) values of the time and amplitude related APs are specified in seconds and signal units (e.g., toco units), respectively, and are listed between the corresponding parentheses. After completing act 201, the process may continue to act 203.

During act 203, the process may obtain a UAS. Accordingly, the process may sense uterine activity signal (UAS). The UAS signal may be acquired and processed on a sample-by-sample basis or in blocks. Illustrative raw UASs such as 402, 502 are shown in FIGS. 4 and 5. Act 203 may be considered a signal acquisition act in which current sample(s) of the UAS(s) are acquired. After completing act 203, the process may continue to act 205.

During act 205, the process may analyze the UAS to determine whether a data stream of the UAS is interrupted, constant, or bad. With regard to an interrupted signal (e.g., an interrupted data stream), a signal may be determined to be interrupted if no new signal data is coming in. The signal (e.g., data stream) may be interrupted, for example, when the (UAS) acquisition device malfunctions or when a connection with the device is (temporarily) lost. Accordingly, the process may analyze the signal to determine whether it has been interrupted. Further, with regard to a constant UAS, the process may determine a UAS is constant if it does not change (significantly, such as more than +/−1% of the full range of the signal over a period of time such as 20 seconds in the present example as indicated in the AP settings Table 2. However, other values are also envisioned. The signal may be constant, for example, when the (UAS) acquisition sensor is disconnected from the patient. Further, with regard to a bad signal, the process may determine that a signal is bad when the sensor is not attached properly to the abdomen of the patient. A bad signal may be detected using any suitable method. For example, the variance of the difference between the (delayed) raw UAS and the cleaned UAS may be used. In addition, if many small peaks (on the UAS) are detected with timing properties quite different from those of contractions, the signal may also be considered bad.

Accordingly, if it is determined that the UAS is interrupted, constant, or bad, the process may determine that the UAS signal is unsuitable, then the process may reset variables during act 209 so that new samples (e.g., next samples or $n^{th}+1$) may be acquired and act 203 may be repeated. However, if it is determined that the UAS is not interrupted, constant, or bad, the process may determine that the UAS signal is suitable and continue to act 207.

During act 207, the process may suppress noise in the UAS. Accordingly, the UAS may be filtered by any suitable filter such as a nonlinear noise suppressor filter (e.g., a weighed order filter or the like such as a (weighted) median, (weighted) order statistic, decision-based, morphological and/or other nonlinear filtering operation performed by any suitable filter. This nonlinear filtering operation is especially suited to suppress (strong) artifacts that are asymmetrically distributed and/or relatively short, but also other kinds of artifacts may be attenuated very effectively. As shown in the diagram, information about the derivative(s) of the cleaned signal, e.g., the (mean) slope, may assist the suppression. The process may form a noise-suppressed UAS and output this signal to a signal smoother as will be described below.

With regard to filters, in accordance with embodiments of the present system, nonlinear artifact suppression filters may be configured for different signal scenarios. For example, because many large artifacts are positive impulse-like signals, it may be advantageous to use one or more nonlinear filters which may take into account temporal and rank order to exploit this and/or other properties of the desired signal and noise. Examples are trimmed mean filters, L-filters, C-filters, M-filters, R-filters, weighted order filters, multi-stage median filters, median hybrid filters, stack filters, polynomial filters, data-dependent filters, decision-based filters and morphological filters. After completing act 207, the process may continue to act 211.

During act 211, the process may perform a smoothing operation using any suitable smoother upon the noise-suppressed UAS to form a smoothed UAS. Accordingly, the process may use a smoothing filter to smooth the noise-suppressed UAS input thereto to smooth this signal and output a smoothed UAS. In accordance with some embodiments, the signal smoother may include a linear finite impulse response (FIR) or infinite impulse response (IIR) filter with a low-pass frequency response, or a nonlinear smoother such as a trimmed mean filter. After completing act 211, the process may continue to act 213.

During act 213, the process may optionally downsample the smoothed UAS signal. With regard to this process, the low-pass filter effect of 211 may act as an anti-aliasing filter. The downsampling may be performed using any suitable downsampler configured in accordance with embodiments of the present system. The signal at this point will be known as the downsampled signal (regardless of whether it was optionally downsampled). After completing act 213, the process may continue to act 215.

During acts 215 and 217, the process may remove changes in baseline offsets from the downsampled signal and determine moving percentiles and perform baseline jump detection. More particularly, during act 215, the process may detect jumps in the baseline offset of the downsampled signal based on the observations that the levels of the downsampled signal before and after the jump differ significantly (for example, greater than +/−15% of the full range of the signal), that the variance of the signal on either side of the jump is relatively small (e.g., less than a threshold variance value, such as +/−5% of the full range of the signal), and that the slope of the signal during the jump is very steep. The process may further estimate the baseline offset by continuously tracking a local percentile (e.g., minimum or 3% percentile) over a certain window of time (e.g., a certain period of time). Several moving percentiles may be computed for assisting other acts of the current process such as the peak detection process of act 227 and/or nonlinear noise suppression process of act 207. After completing act 215, the process may continue to act 217.

During act 217, the process may subtract the baseline offset determined during act 215 from the downsampled signal and form a corresponding cleaned signal. The subtraction may be performed using any suitable combiner (e.g., an adder, subtractor, etc.). After completing act 217, the process may continue to act 219.

During act 219, the process may compute derivative(s) of the cleaned signal with respect to time. This may be performed using FIR or IIR derivative filters or some other numerical differentiator (e.g., based on Savitsky-Golay filtering or the like) to determine the derivatives of the cleaned signal. After completing act 219, the process may continue to act 221.

During act 221, the process may compute smoothing parameter(s) from the cleaned signal and/or its derivative(s) (e.g., computed during act 219) which allows for the computation of a threshold signal that follows the cleaned signal in a controlled and desired manner. The smoothing parameter(s) should be determined so that in the ascending part of a contraction the threshold signal follows the cleaned signal quickly in the sense that it can increase at almost the same amount per time unit and that it is delayed a bit with respect to it. However, in the descending part of the contraction, the smoothing parameter(s) should be determined so that the threshold signal follows the cleaned signal slowly so as to avoid detection of small local peaks by the process. After completing act 221, the process may continue to act 223.

During act 223, the process may perform signal-dependent smoothing of the cleaned UAS signal so as to form a threshold signal. More particularly, the signal dependent smoothing of the cleaned signal, which yields the threshold signal, may be performed in accordance with the signal dependent smoothing parameter(s) computed during act 221. After completing act 223, the process may continue to act 225.

During act 225, the process may impose a minimum on the threshold signal. The minimum may be imposed on the threshold signal to avoid false detections due to remaining small peaks and noise. The threshold signal is now ready to be analyzed by a peak detector state machine. After completing act 225, the process may continue to act 227.

During act 227, the process may detect peaks using the PDSM which may receive information such as one or more of the cleaned signal, the threshold signal, the derivative signal(s), the moving percentiles and the baseline jump information. More particularly, the PDSM may determine one or more states such as an outside contraction, start of contraction, ascending part of contraction, peak of contraction, peak decision, descending part of contraction, end of contraction, and/or abort (of contraction) based upon the received information. A process performed by a PDSM such as a peak detector state machine is illustrated with reference to FIG. 3. In accordance with embodiments of the present system, the PDSM may provide information which it generates using a graphics engine. After completing act 227, the process may continue to act 229 and may repeat act 203, as desired.

During act 229 the process may generate content based upon the information input to the graphics engine. More particularly, the graphics engine may determine and form content which corresponds with the USPS and which may be formed in accordance with a selected theme and/or color to be rendered as discussed above with reference to act 111 of process 100. After completing act 229, the process may continue to act 231. During act 231, the process may render the content using any suitable method such as a display, a projector, a speaker, a haptic device, etc. In accordance with embodiments of the present system, acts 229, 231 may be run continuously, periodically and/or on any other type of schedule as desired.

In accordance with yet other embodiments of the present system, the process may use expert knowledge/CDS systems. For example, in some embodiments, the process may compare uterine activity information with threshold information and perform certain actions based upon the results of the comparison. For example, if it is determined that the magnitude of a signal corresponding to uterine activity exceeds a threshold value, the process may administer medication (e.g., at a default or determined amount, base upon system settings) and/or sound an alarm based upon system settings. Thus, embodiments of the present system may employ, CDS methods to, for example, administer medication and/or trigger alarms when appropriate.

Further, pattern recognition may be applied to the cleaned signal to differentiate contractions by type such as final contraction(s) from normal contraction(s), if desired. Accordingly, the process may determine whether a contraction is normal or final and may render results of the determination.

Figure 3:
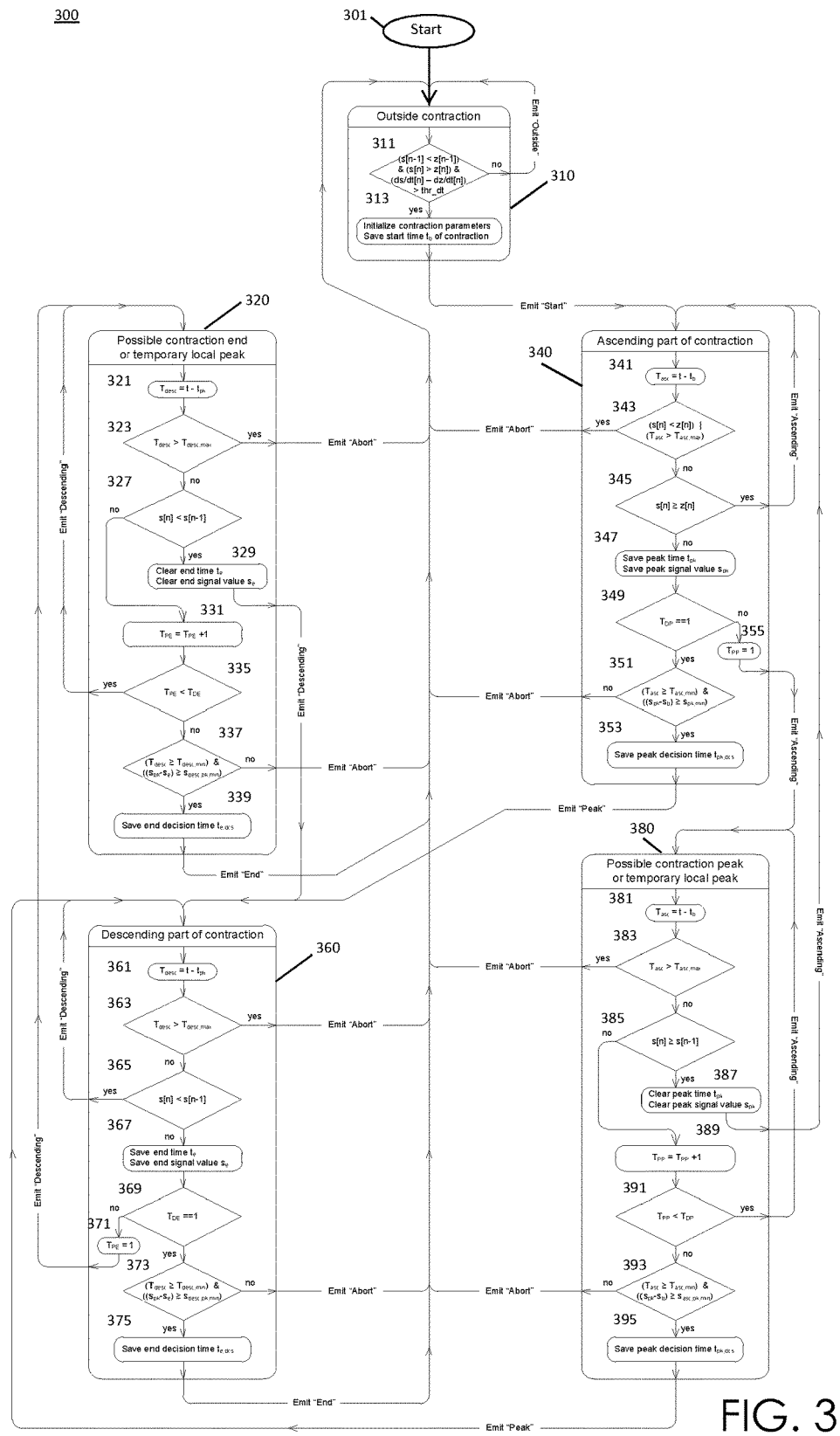
FIG. 3 is a flow diagram that illustrates a process performed by a Peak Detector State Machine (PDSM) in accordance with embodiments of the present system.

FIG. 3 is a flow diagram that illustrates a process 300 performed by a PDSM in accordance with embodiments of the present system.

The process 300 may be performed using one or more computers that may communicate over a network and may obtain information from, and/or store information to one or more memories which may be local and/or remote from each other. The process 300 may include one of more of the following acts. Further, one or more of these acts may be combined and/or separated into sub-acts, if desired. Moreover, one or more of these acts may be skipped depending upon settings. The process 300 may include one or more functional blocks 310, 320, 340, 360, and 380 which may determine whether an outside contraction is detected; a contraction end or temporary local peak is detected; an ascending part of contraction is detected; a descending part of contraction is detected; and a possible contraction peak or temporary local peak is detected; respectively. Further, in each of these states the process may emit at least a part of the parameter information as will be discussed below. In operation, the process may start during act 301 and then proceed to act 311. Parameters emitted by the process 300 may correspond with information related to the USPS. Further, during process 300 a condition may be determined to be satisfied if it is found to be true. Conversely, a condition may be determined not to be satisfied if it is determined to be false. The process 300 may further store information that it acquires, generates or otherwise uses for later use. For example, start, peak and/or end times of contractions may be stored for comparison to, for example, determine whether a first contraction is larger than a later contraction, etc. As used in the acts of process 300 words (e.g., "outside," "start," etc.) emitted during the acts refer to parameter or states as may be included in the USPS.

Functional Block 310

During act 311, the process may determine whether the condition ($s[n-1]<z[n-1]$) and ($s[n]>z[n]$) and (($ds/dt[n]-dz/dt[n]$)>thr_dt) is satisfied. Accordingly, if this condition is satisfied, the process may continue to act 313. However, if this condition is not satisfied (e.g., negative), the process may emit "outside," and may thereafter repeat act 311. As used herein: $s[n]$ is a cleaned signal at time index n; $s[n-1]$ is cleaned signal at time index n−1; $z[n]$ is a threshold signal at time index n; and $z[n-1]$ is a threshold signal at time index n−1.

During act 313, the process may initialize contraction parameters for a current contraction, may reset and/or save a start time $t_b$ of the current contraction and may emit "start." After completing act 313, the process may continue to functional block 340 starting with act 341

Functional Block 340

During act 341, the process may set $T_{asc}=t-t_b$. Then, the process may continue to act 343.

During act 343, the process may determine whether the condition (($s[n]<z[n]$)|($T_{asc}=T_{asc\_max}$)) is satisfied. Accordingly, if this condition is satisfied (e.g., answered in the affirmative), the process may emit "Abort" and may repeat act 311. The "Abort" may be defined as the decision that a candidate contraction, the first part of which appeared to be contraction, turns out not to be a contraction after all (e.g. it was an artifact).

However, if this condition is not satisfied, the process may continue to act 345.

During act 345, the process may determine whether the condition ($s[n]<z[n]$) is satisfied. Accordingly, if it is determined that this condition is satisfied, the process may emit "Ascending" as parameter information and may repeat act 341. However, if is determined that this condition is not satisfied, the process may continue to act 347.

During act 347, the process may save a peak time $t_{pk}$ which is indicative of a time at which a peak occurs and may save a peak signal value $S_{pk}$. After completing act 347, the process may continue to act 349.

During act 349, the process may determine whether the condition ($T_{DP}=1$). Accordingly, if it is determined that this condition is satisfied, the process may continue to act 351. However, if is determined that this condition is not satisfied, the process may continue to act 355.

During act 355, the process may set Tpp=1, and emit "Ascending" and thereafter continue to functional block 380 starting with act 381.

During act 351, the process may determine whether the condition ($T_{asc}>=T_{asc,min}$) & (($S_{pk}-S_b$)>=$S_{pk,min}$) is satisfied. Accordingly, if it is determined that this condition is satisfied, the process may continue to act 353. However, if is determined that this condition is not satisfied, the process may emit "Abort" and repeat act 311.

During act 353, the process may save the peak decision time $t_{pk,dcs}$. After completing act 353, the process may emit "Peak" and continue to functional block 360 starting with act 361.

Functional Block 360

During act 361, the process may set $T_{desc}=t-t_{pk}$ and thereafter continue to act 363. During act 363, the process may determine whether the condition ($T_{desc}>T_{esc,max}$) is satisfied. Accordingly, if this condition is satisfied, the process may emit "Abort" repeat act 311. However, if this condition is not satisfied, the process may continue to act 365.

During act 365, the process may determine whether the condition ($s[n]<s[n-1]$) is satisfied. Accordingly, if it is determined that this condition is satisfied, the process may emit "Descending" and thereafter repeat act 361. However, if this condition is not satisfied, the process may continue to act 367.

During act 367, the process may save an end time $t_e$ and/or save an end signal value $s_e$. After completing act 367, the process may continue to act 369.

During act 369, the process may determine whether the condition ($T_{DE}=1$) is satisfied. Accordingly, if it is determined that this condition is satisfied, the process may continue to act 371. However, if this condition is not satisfied, the process may continue to act 373.

During act 371, the process may set $T_{PE}=1$, emit "Descending" and thereafter continue to functional block 320 starting with act 321.

During act 373, the process may determine whether the condition (($T_{desc}>=T_{des,min}$) & (($S_{pk}-S_e$)>=$S_{desc,pk,min}$)) is satisfied. Accordingly, if it is determined that this condition is satisfied, the process may continue to act 375. However, if is determined that this condition is not satisfied, the process may emit "Abort" and repeat act 311.

During act 375, the process may save an end decision time $t_{e,dcs}$. After completing act 375, the process may emit "End" and repeat act 311.

Functional Block 320

During act 321, the process may set $T_{desc}=t-t_{pk}$ and thereafter continue to act 323. During act 323, the process may determine whether the condition ($T_{desc}>T_{desc,max}$) is satisfied. Accordingly, if this condition is satisfied, the process may emit "Abort" and may thereafter repeat act 311. However, if this condition is not satisfied, the process may continue to act 327.

During act 327, the process may determine whether the condition ($s[n]<s[n-1]$) is satisfied. Accordingly, if it is determined that this condition is satisfied, the process may continue to act 329. However, if this condition is not satisfied, the process may continue to act 331.

During act 329, the process may clear an end time $t_e$ and clear an end signal value $S_e$. After completing act 329, the process may emit "Descending" and may thereafter continue to act 361. During act 331, the process may set $T_{PE}=T_{PE}+1$. After completing act 331, the process may continue to act 335.

During act 335; the process may determine whether the condition ($T_{PE}<T_{DE}$) is satisfied. Accordingly, if it is determined that this condition is satisfied, the process may emit "Descending" and may thereafter repeat act 321. However, if this condition is not satisfied, the process may continue to act 337.

During act 337, the process may determine whether the condition (($T_{desc}>=T_{decs,min}$) & (($S_{pk}-S_e$)$>=S_{desc,pk,min}$)) is satisfied. Accordingly, if it is determined that this condition is satisfied, the process may continue to act 339. However, if is determined that this condition is not satisfied, the process may emit "Abort" and repeat act 311.

During act 339, the process may save an end decision time $t_{e,dcs}$. After completing act 339, the process may emit "End" and repeat act 311.

Functional Block 380

During act 381, the process may set $T_{asc}=t-t_b$ and thereafter continue to act 383. During act 383, the process may determine whether the condition ($T_{asc}>T_{asc,max}$) is satisfied. Accordingly, if this condition is satisfied, the process may emit "Abort" and may thereafter repeat act 311. However, if this condition is not satisfied, the process may continue to act 385.

During act 385, the process may determine whether the condition (s[n]>=s[n-1]) is satisfied. Accordingly, if it is determined that this condition is satisfied, the process may continue to act 387. However, if this condition is not satisfied, the process may continue to act 389.

During act 387, the process may clear a peak time $t_{pk}$ and clear a peak signal $s_{pk}$. After completing act 329, the process may emit "Ascending" and may thereafter repeat act 341.

During act 389, the process may set $T_{PP}=T_{PP}+1$. After completing act 389, the process may continue to act 391. During act 391, the process may determine whether the condition ($T_{PP}<T_{DP}$) is satisfied. Accordingly, if it is determined that this condition is satisfied, the process may emit "Ascending" and may thereafter repeat act 381. However, if this condition is not satisfied, the process may continue to act 393.

During act 393, the process may determine whether the condition (($T_{asc}>=T_{asc,min}$) & (($S_{pk}-S_b$)$>=S_{asc,pk,min}$)) is satisfied. Accordingly, if this condition is satisfied, the process may continue to act 395. However, if this condition is not satisfied, the process may emit "Abort" and thereafter repeat act 311. During act 395, the process may save a peak decision time $t_{pk,dcs}$. After completing act 395, the process may emit "Peak" as parameter information and continue to act 361.

The emitted parameter information may then be transmitted to the graphics engine for further processing in accordance with embodiments of the present system.

In yet other embodiments, the process may determine a baseline offset for a UAS and adjust the baseline offset if it is determined to run off scale or beyond threshold limits. Further, if the UAS is determined to run off scale, the process may automatically scale the UAS, if desired, so that the UAS is no longer off scale. The process may further adjust time delay so as to enhance signal detection reliability.

Embodiments of the present system may provide clinical decision support (CDS) for the convenience of a user such as a patient and/or professional. For example, it is envisioned that all uterine activity data that is acquired during the labor process may be logged/saved to a memory of the system such as a disc storage device, a non-transitory memory, and/or any other (future) data storage technology that may provide for offline usage. This data may then be used for example to provide items in a visual representation (e.g., information items) for example obtained after online or offline processing, representing contractions of the user (e.g. flowers, plants, balloons, etc.). In accordance with embodiments of the present system, the items may be annotated with information about the corresponding contractions/events such as a timestamp indicating a time at which the corresponding contractions occurred, the duration and/or intensity. This may also be performed in an interactive manner. For example, items in the visual representations of contractions (such as the flowers) might be made selectable (e.g., by clicking) and/or "zoomable". Then, for example, when the user selects an information item or portion thereof about a corresponding contraction, related information about the contraction such as time (e.g., time of occurrence), duration and intensity, might be displayed on the screen. This functionality may significantly help in recalling events (and their properties) that occurred during labor ("Indeed, at 12:13 hrs I was having such strong contractions . . . "). This forms a kind of "post-birth-care" or post-birth recollection of (strong and/or nice) memories.

The uterine activity data may be used to (re-)process the data (the signal processing parameters and/or algorithm might be adjusted), which may provide better results when processed offline, and/or to obtain a different visualization (or even multiple visualizations) by adjusting, for example, visualization parameters. The uterine activity data may be used to (re-)process the data to obtain a different visualization (theme) by applying a different mapping, e.g. one that maps the extracted UA parameters to a garden of plants/trees instead of a tree, or a set of balloons. In accordance with the present system, the visual representation is provided as a visual metaphor for the data so that the data may be easily comprehended without a need to analyze or review the details of the data directly. This metaphor is provided in the form of the mapping of the data to visual elements, such as the length of a contraction may be mapped to a size of a leaf, a time between contractions may be mapped a distance between leaves, etc. These mapping may be provided in a form of a selectable theme (e.g., leaves, balloons, etc.).

It is also envisioned that any conceivable mapping(s) may be used and might be tuned by the user, also in the online/real-time application of the method. Even a cleaned signal itself, possibly overlaid with the extracted parameters and/or states may be displayed. Offline, even different visualizations may be made if, for example, the user desires to do so. Further, patients, spouses, and/or professionals may also like a summary of the statistics of the various events, such as the total number of contractions and/or the average frequency of the contractions. This information may for example be provided in a home monitoring situation. Further, this information may be transmitted to a health provider, etc. Home-based monitoring including labor is possible with the devices, methods and computer programs of the instant application, but so too for other healthcare fields that are characterized by long-term processes, treatments and/or monitoring. The instant inventions can be relevant in complex contexts where different physiological parameters are collected and patients undergo physically unpleasant and/or emotionally tough experiences, and this kind of data visualization feedback can help improve the patient experience and/or treatment by providing additional insight to the patient and caregiver as well as positive encouragement in a more understandable and comforting manner. By all means, not meant to limit the invention of the present application, other examples where these devices, methods and computer programs of the invention could be utilized include oncology patients receiving chemotherapy, kidney dialysis patients receiving (hemo)dialysis treatment, diabetic patients monitoring control of their glucose, monitoring in women experiencing (unexplained) infertility problems, and/or monitoring of intensive care patients by providing data visualization as feedback for family.

With regard to the process 300, this process may be performed by a finite state machine (FSN) which may transition between a finite number of states such as may be represented by functional blocks 310, 320, 340, 360 and 380.

Referring to act 311 of functional block 310, this functional block may represent an "Outside contraction" (e.g., outside of uterine contraction state). During process 300, the cleaned signal s[n] may include one or more different parts. At any given point in time (t), the FSM may be either in a (uterine) contraction state or not. Accordingly, a state of the FSM that is referred to as an "Outside contraction" represents a state of the system when not in a (uterine) contraction state (e.g., outside of a uterine contraction) and may be represented by the functional block 310. Clearly, when in the "Outside contraction" state the process may only stay there until the proper conditions (e.g., of act 311) are satisfied. Once these conditions are satisfied, the process may transition to a state that is called "Ascending part of contraction," as represented by functional block 340, which represents an ascending part of a uterine contraction. Thus, as shown in the PDSM diagram of FIG. 3, act 311 lists 3 conditions that should be satisfied in order to transition to the "Ascending part of contraction" state as represented by functional block 340. The first condition requires that at a previous time index n−1, the cleaned signal s should be less than the threshold signal z, and the second condition requires that at the current time index n, the cleaned signal s should be greater than the threshold signal z. These first two conditions thus represent the crossing of the threshold z by the cleaned signal s, thereby signifying the start of a uterine contraction candidate. In order to assure that it is the start of a proper uterine contraction and not just a small and slow bump, a third condition requires that a time derivative of s minus a time derivative of z should be greater than a tunable threshold, so that bumps in s that rise sufficiently fast are retained and small local bumps are eliminated (there should be a sufficiently large differences in the slopes of s and z). Then, during act 313, among other things, the process may record the time at which the potential uterine contraction starts and also the corresponding value of s.

The reasoning for the other functional blocks and corresponding states is generally similar. For example, given any state, at several points in time t, the process may determine whether it is still in a "proper contraction" and may therefore perform several determinations to ascertain such. For example, at several points in time, an "ascending time" $T_{asc}$ may be computed as the difference between a current time and a start time of a current peak/contraction. Likewise, a descending time $T_{desc}$ from the peak time until the current time may be computed. Both values may obviously be restricted to intervals observed in clinical practice. These intervals may be defined by $[T_{asc,min}, T_{asc,max}]$ for the ascending time and $[T_{desc,min}, T_{desc,max}]$ for the descending time. If these times do not lie in a proper interval, the current contraction candidate is "aborted" and the process returns to the "Outside contraction" state of block 310 at act 311. Other conditions that may need to be determined are whether the current peak values are sufficiently large, this determination may be performed, for example, during acts 351 and 393 (where $s_{pk}$ is a value of s at the peak, and $s_b$ is a value of s at a start of a corresponding contraction). When in an ascending part of a contraction, there may be small local peaks which are undesirable for consideration such as a main peak of the contraction. Therefore, when the uterine activity signal descends after a possibly local maximum is detected, the process may wait for a "Peak decision time" $T_{DP}$ to determine whether the uterine activity signal starts ascending/increasing again ($T_{PP}$ keeps track of the time spent in a Possible Peak). If this condition is determined to occur, the process may remain in the ascending state. If not, the process may determine whether this latest peak is a true peak or not. This act may be performed during acts 351 and 393.

It should be expressly understood that these and other acts described herein are intended merely as an illustration of how these states and others may be determined. Other acts, algorithms, parameters, etc. would readily occur to a person of ordinary skill in the art and are intended to be encompassed by the description of the present system.

Figure 9:
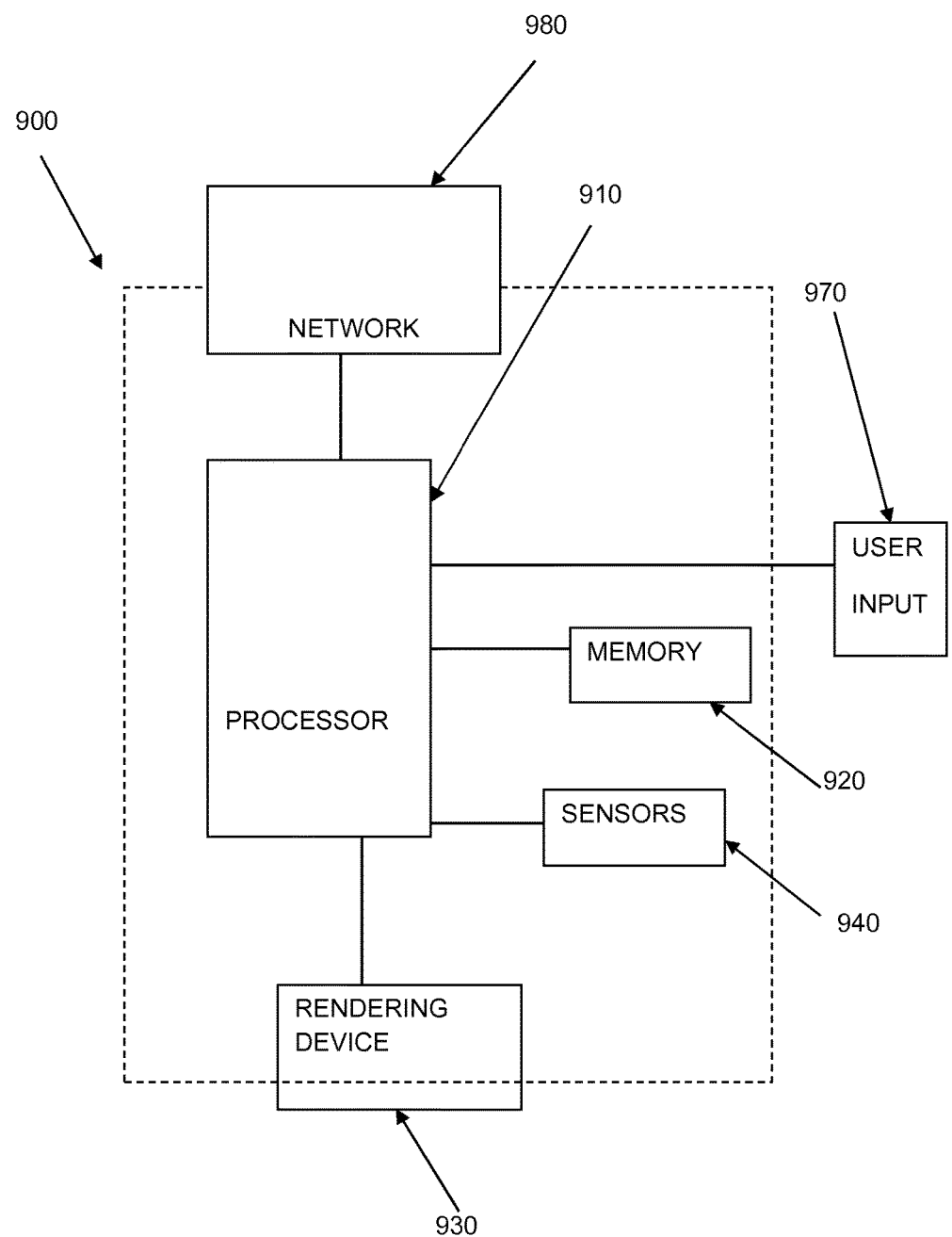
FIG. 9 shows a portion of a system in accordance with embodiments of the present system.

FIG. 9 shows a portion of a system 900 in accordance with an embodiment of the present system. For example, a portion of the present system 900 may include a processor 910 (e.g., a controller) operationally coupled to a memory 920, a user interface 930, sensors 940, and a user input device 970. The memory 920 may be any type of device for storing application data as well as other data related to the described operation. The application data and other data are received by the processor 910 for configuring (e.g., programming) the processor 910 to perform operation acts in accordance with the present system. The processor 910 so configured becomes a special purpose machine particularly suited for performing in accordance with embodiments of the present system. The sensors may include, for example, sensors to detect uterine activity of a patient such as a toco, IPC and/or an EHG device, etc.

The operation acts may include configuring the system 900 by, for example, configuring the processor 910 to obtain information from user inputs, the sensors 940, and/or the memory 920 and processing this information in accordance with embodiments of the present system to obtain information related to uterine activity of a patient which may form at least part of UAS information in accordance with embodiments of the present system. The user input portion 970 may include a keyboard, a mouse, a trackball and/or other device, including touch-sensitive displays, which may be stand alone or be a part of a system, such as part of a personal computer, a notebook computer, a netbook, a tablet, a smart phone, a personal digital assistant (PDA), a mobile phone, and/or other device for communicating with the processor 910 via any operable link. The user input portion 970 may be operable for interacting with the processor 910 including enabling interaction within a UI as described herein. Clearly the processor 910, the memory 920, the UI 930 and/or user input device 970 may all or partly be a portion of a computer system or other device such as a client and/or server as described herein.

Operation acts may include requesting, providing, forming and/or rendering of information such as, for example, information related to uterine activity of a patient. The processor 910 may render the information on the UI 930 such as on a display of the system. The sensors may further include suitable sensors to provide desired sensor information to the processor 910 for further processing in accordance with embodiments of the present system.

The methods of the present system are particularly suited to be carried out by processor programmed by a computer software program, such program containing modules corresponding to one or more of the individual steps or acts described and/or envisioned by the present system.

The processor 910 is operable for providing control signals and/or performing operations in response to input signals from the user input device 970 as well as in response to other devices of a network and executing instructions stored in the memory 920. For example, the processors 910 may obtain feedback information from the sensors 940 and may process this information to produce a user interface and renderings as described herein. The processor 910 may include one or more of a microprocessor, an application-specific or general-use integrated circuit(s), a logic device, etc. Further, the processor 910 may be a dedicated processor for performing in accordance with the present system or may be a general-purpose processor wherein only one of many functions operates for performing in accordance with the present system. The processor 910 may operate utilizing a program portion, multiple program segments, or may be a hardware device utilizing a dedicated or multi-purpose integrated circuit.

Accordingly, embodiments of the present system provide one or more algorithms for automatically analyzing a uterine activity signal such as may be acquired using a toco, IUPC, and/or EHG devices. Obstetrical and/or and gynecological information about uterine activity such as the start, peak and end times of contractions, as well as the time intervals between them, their durations, intensities, timing patterns, waveform shapes, and so forth, may be determined and thereafter used to generate a graphical representation for the convenience of users and/or patients.

Accordingly, embodiments of the present system may include two parts: (1) an algorithm for automatically analyzing a uterine activity signal such as obtained with a conventional toco, IUPC, and/or an EHG device in real-time or an offline mode and may form corresponding information; and (2) a particular application of the information provided by the algorithm may render information to enhance women's labor and delivery experience in the hospital by means of properly timed breathing support, and/or visualization of the state and progress of the labor process. Further, embodiments of the present system may further use information provided by embodiments of the present system to provide renderings that facilitate an interactive birthing process which may provide a more positive labor and/or delivery experience to the expectant. Embodiments of the present system may provide an environment which provides guidance in a personal and unobtrusive manner to an expectant mother during the labor process. This guidance may include rendering information that visualizes the labor process and/or assists with a breathing process (e.g., inhalation) of the expectant mother.

In general, because various parameters related to contractions, such as their height and the time intervals between them, can vary a lot the detection of the start, peak and end times is very difficult to perform automatically in (near) real-time. Therefore, whatever input signal representative of the contractions is used, any algorithm for automatically extracting those parameters requires a sophisticated peak detector for obtaining reliable detections. The reliability with which contractions can be detected among other things depends on how much delay is allowed. The presented algorithm contains a peak detector in which explicit trade-offs can be made between the allowed processing and detection delay on the one hand, and the reliability of the results on the other.

Additionally, the algorithm allows explicit trade-offs to be made between:
 The allowed processing and detection delay on the one hand, and the reliability of the extracted parameters on the other; in offline mode, almost perfect analysis is possible;
 The signal level above and at which the start of a contraction is detected, and the number of false and/or aborted detections.

Furthermore, among other things, the various parameters allow the explicit trade-off between time between possible peak detection and definite peak decision on the one hand, and reliability of peak decision on the other.

Further variations of the present system would readily occur to a person of ordinary skill in the art and are encompassed by the following claims.

Finally, the above-discussion is intended to be merely illustrative of the present system and should not be construed as limiting the appended claims to any particular embodiment or group of embodiments. Thus, while the present system has been described with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

In interpreting the appended claims, it should be understood that:
 a) the word "comprising" does not exclude the presence of other elements or acts than those listed in a given claim;
 b) the word "a" or "an" preceding an element does not exclude the presence of a plurality of such elements;
 c) any reference signs in the claims do not limit their scope;
 d) several "means" may be represented by the same item or hardware or software implemented structure or function;
 e) any of the disclosed elements may be comprised of hardware portions (e.g., including discrete and integrated electronic circuitry), software portions (e.g., computer programming), and any combination thereof;
 f) hardware portions may be comprised of one or both of analog and digital portions;
 g) any of the disclosed devices or portions thereof may be combined together or separated into further portions unless specifically stated otherwise;
 h) no specific sequence of acts or steps is intended to be required unless specifically indicated; and
 i) the term "plurality of" an element includes two or more of the claimed element, and does not imply any particular range of number of elements; that is, a plurality of elements may be as few as two elements, and may include an immeasurable number of elements.

The invention claimed is:

1. A uterine activity analysis apparatus, the apparatus comprising:
 a display; and
 at least one controller configured to:

continuously monitor uterine activity information of a patient during a time period by:
  acquiring, via one or more sensors, a uterine activity signal corresponding to uterine activity of the patient during the time period, and
  determining, during the time period, the uterine activity information based upon the acquired uterine activity signal, the uterine activity information comprising information related to at least one parameter of the acquired uterine activity signal being indicative of a contraction,
provide, via the display, an animated breathing guide configured to indicate to the patient when to inhale and exhale; and
continuously update, during the time period, the animated breathing guide based on the continuously monitored uterine activity information,
wherein the animated breathing guide comprises a series of animated components configured to increase in size to indicate inhalation and decrease in size to indicate exhalation.

2. The apparatus of claim 1, wherein the animated breathing guide is automatically synchronized to the patient's contractions based on the continuously monitored uterine activity signal to continuously update the animated breathing guide during the time period.

3. The apparatus of claim 1, wherein the series of animated components is a series of animated roundels configured to increase in size to indicate inhalation and decrease in size to indicate exhalation.

4. The apparatus of claim 1, wherein the at least one parameter comprises a threshold signal, a derivative signal with respect to time, a moving percentile, a baseline offset, and/or a cleaned signal.

5. The apparatus of claim 4, wherein the at least one controller is further configured to determine the uterine activity information by:
  continuously tracking a local percentile over the time period; and
  estimating the baseline offset based on the continuously tracked local percentile.

6. The apparatus of claim 5, wherein the at least one controller is further configured to determine the uterine activity information further by:
  generating, via a signal smoother, a smoothed uterine activity signals during the time period based on the continuously acquired uterine activity;
  removing the baseline offset from the smoothed uterine activity signal to obtain the cleaned signal; and
  determine, during the time period, the uterine activity information based on the cleaned signal.

7. The apparatus of claim 5, wherein the at least one controller is further configured to determine the uterine activity information by:
  determining, based on the at least one parameter, contraction state information, the contraction state information comprising an outside contraction, a start of the outside contraction, an ascending part of the outside contraction, a peak time of the outside contraction, a descending part of the outside contraction, an end time of the outside contraction, time between two contractions, and/or a duration of the outside contraction.

8. The apparatus of claim 7 wherein the at least one controller is further configured to:
  continuously update the animated breathing guide by controlling movement of an animated component of the series of the animated components relative to other animated components of the series of the animated components based on the contraction state information.

9. The apparatus of claim 8, wherein a distance between two or more animated components of the series of animated components indicates time between two contractions.

10. The apparatus of claim 8, wherein a size of at least one animated component of the series of animated components indicates a duration of the patient's contractions.

11. The apparatus of claim 1, wherein the at least one controller is further configured to:
  determine whether a magnitude of the uterine activity information reaches a threshold value; and
  responsive to the threshold value being reached, causing a medication to be administered to the patient.

12. The apparatus of claim 1, wherein the apparatus comprises the one or more sensors.

13. The apparatus of claim 1, wherein continuously monitoring the uterine activity information comprises periodically acquiring the uterine activity signal via the one or more sensors during the time period.

14. A method for uterine activity analysis and providing interactive guidance during labor and delivery, the method comprising:
  continuously monitoring, via one or more physical processor, uterine activity information of a patient during a time period by:
    acquiring, via one or more sensors, a uterine activity signal corresponding to uterine activity of the patient during the time period, and
    determining, during the time period, the uterine activity information based upon the acquired uterine activity signal, the uterine activity information comprising information related to at least one parameter of the acquired uterine activity signal being indicative of a contraction;
  providing, via a display, an animated breathing guide configured to indicate to the patient when to inhale and exhale; and
  continuously updating, via the one or more physical processor, the animated breathing guide based on the continuously monitored uterine activity information,
  wherein the animated breathing guide comprises a series of animated components configured to increase in size to indicate inhalation and decrease in size to indicate exhalation.

15. The method of claim 14, wherein the animated breathing guide is automatically synchronized to the patient's contractions based on the continuously monitored uterine activity signal to continuously update the animated breathing guide during the time period.

16. The method of claim 14, wherein the series of animated components is a series of animated roundels configured to increase in size to indicate inhalation and decrease in size to indicate exhalation.

17. The method of claim 14, further comprising:
  continuously updating the animated breathing guide by controlling movement of an animated component of the series of the animated components relative to other animated components of the series of the animated components based on the contraction state information.

18. The method of claim 17, wherein a distance between two or more animated components of the series of animated components indicates time between two contractions.

19. The method of claim 17, wherein a size of at least one animated component of the series of animated components indicates a duration of the patient's contractions.

20. A system for uterine activity analysis and providing interactive guidance during labor and delivery, the system comprising:
- a display; and
- at least one controller configured to:
    - continuously monitor uterine activity information of a patient during a time period by:
        - acquiring, via one or more sensors, a uterine activity signal corresponding to uterine activity of the patient during the time period,
        - determining, during the time period, the uterine activity information based upon the acquired uterine activity signal, the uterine activity information comprising information related to at least one parameter of the acquired uterine activity signal being indicative of a contraction, and
        - determining, based on the at least one parameter, contraction state information, the contraction state information comprising an outside contraction, a start of the outside contraction, an ascending part of the outside contraction, a peak time of the outside contraction, a descending part of the outside contraction, an end time of the outside contraction, time between two contractions, and/or a duration of the outside contraction;
    - provide, via the display, an animated breathing guide configured to indicate to the patient when to inhale and exhale, the animated breathing guide being provided as a set of animated components; and
    - continuously update, during the time period, the animated breathing guide based on the continuously monitored uterine activity information by controlling movement of an animated component of the set of the animated components relative to other animated components of the set of the animated components based on the contraction state information,
    - wherein a distance between two or more animated components of the set of animated components indicates time between two contractions.

21. The system of claim 20, wherein the animated breathing guide is automatically synchronized to the patient's contractions based on the continuously monitored uterine activity signal to continuously update the animated breathing guide during the time period.

* * * * *